(12) United States Patent
Chazalet et al.

(10) Patent No.: US 6,417,216 B1
(45) Date of Patent: Jul. 9, 2002

(54) FUNGICIDAL COMPOSITION COMPRISING A 2-IMIDAZOLIN-5-ONE

(75) Inventors: Maurice Chazalet, Anse; Marie-Pascale Latorse, Sourcieuz les Mines; Richard Mercer, Ecully, all of (FR)

(73) Assignee: Aventis CropScience, S.A., Lyons (FR)

( * ) Notice: Subject to any disclaimer, the term of this patent is extended or adjusted under 35 U.S.C. 154(b) by 0 days.

(21) Appl. No.: 09/043,825

(22) PCT Filed: Dec. 30, 1997

(86) PCT No.: PCT/FR97/02449

§ 371 (c)(1),
(2), (4) Date: Feb. 22, 2000

(87) PCT Pub. No.: WO93/24467

PCT Pub. Date: Dec. 9, 1993

(51) Int. Cl.[7] .......................... A01N 43/50; A01N 37/18
(52) U.S. Cl. ........................................ 514/386; 514/617
(58) Field of Search .................................. 514/386, 617

(56) References Cited

U.S. PATENT DOCUMENTS 5,906,986 A    5/1999   Latorse ....................... 514/141

FOREIGN PATENT DOCUMENTS

| EP | 0 600 629 A1 | 11/1993 |
| EP | 0 753 258 A2 A3 | 1/1997 |
| FR | WO 96/03044 | 2/1996 |

OTHER PUBLICATIONS

English language Abstract of WO 96/03044 (Feb. 8, 1996) (from Orbit).

*Primary Examiner*—Allen J. Robinson
(74) *Attorney, Agent, or Firm*—Connolly Bove Lodge and Hutz LLP

(57) ABSTRACT

1) Fungicidal compositions comprising a compound (I) which is preferably (4S)-4-methyl-2-methylthio-4-phenyl-1-phenylamino-2-imidazolin-5-one and a compound (II) which is N-[3'-(1'-chloro-3'-methyl-2'-oxopentan)]-3,5-dichloro-4-methylbenzamide;

the compound (I)/compound (II) ratio by weight being from 0.01 to 50, preferably from 0.1 to 10.

2) Process for curatively or preventively combating the phytopathogenic fungi of crops, characterised in that an effective and non-phytotoxic amount of a fungicidal composition is applied to the vegetation to be treated.

19 Claims, No Drawings

FUNGICIDAL COMPOSITION COMPRISING A 2-IMIDAZOLIN-5-ONE

Novel fungicidal composition comprising a 2-imidazolin-5-one

This application a 371 of PCT/FR 97/02449, Filed Dec. 30, 1997.

The present invention relates to novel fungicidal compositions comprising a 2-imidazolin-5-one, which are intended in particular for protecting crops. The invention also relates to a process for protecting crops against fungal diseases.

Compounds derived from 2-imidazolin-5-ones with fungicidal action are known, in particular from European patent application EP 551,048, these compounds making it possible to prevent the growth and development of phytopathogenic fungi which attack or are liable to attack crops.

International patent application WO 96/03044 also discloses a certain number of fungicidal compositions comprising a 2-imidazolin-5-one in combination with one or more fungicidal active materials.

However, it is always desirable to improve the products which can be used by growers in order to combat fungal diseases of crops, and in particular mildews.

It is also always desirable to reduce the doses of chemical products spread into the environment to combat fungal attacks on crops, in particular by reducing the application doses of the products.

It is also always desirable to increase the number of antifungal products available to growers in order that they will find, among these products, the one which is best suited to the grower's specific use.

One aim of the invention is thus to provide a novel fungicidal composition which is useful for the problems outlined above.

Another aim of the invention is to propose a novel fungicidal composition which is useful in the preventive and curative treatment of Solanacea diseases.

Another aim of the invention is to propose a novel fungicidal composition which is of improved efficacy against mildew and/or early blight in Solanaceae.

Another aim of the invention is to propose a novel fungicidal composition which is of improved efficacy against mildew and/or oidium and/or botrytis in grapevine.

It has now been found that these aims may be achieved, partly or totally, by means of the fungicidal compositions according to the present invention.

The subject of the present invention is thus, firstly, fungicidal compositions comprising a compound (I) of formula:

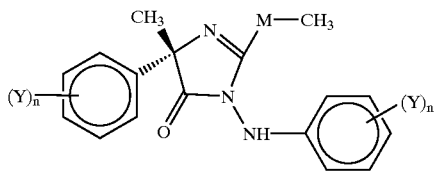

(I)

in which:
M represents an oxygen or sulphur atom;
n is an integer equal to 0 or 1;
Y is a fluorine or chlorine atom or a methyl radical;
and a compound (II) which is N-[3'-(1'-chloro-3'-methyl-2'-oxopentan)]-3,5-dichloro4-methylbenzamide;
the compound (I)/compound (II) ratio by weight being from 0.01 to 50, preferably from 0.1 to 10.

The compositions according to the invention are advantageous for combating, in particular, mildews of the Solanaceae, such as potatoes or tomatoes, as well as for combating mildew and oidium of grapevine.

Compound (I) is known, in particular from patent application EP 629,616.

Compound (II) and its use as a fungicide are described in European patent application EP 600,629.

The compound (I)/compound (II) ratio is defined as being the ratio of the weight of these 2 compounds. This is likewise the case for any ratio of 2 chemical compounds, mentioned below in the present text, insofar as a definition different from this ratio is not expressly indicated.

These compositions generally appreciably improve the respective and isolated action of compound (I) and of compound (II) for a number of fungi that are particularly harmful in crops, in particular for Solanaceae, more particularly for mildew of Solanaceae while at the same time retaining an absence of phytotoxicity towards these crops. This therefore results in an improvement in the spectrum of activity and the possibility of decreasing the respective dose of each active material used, the latter quality being particularly advantageous for readily appreciated ecological reasons.

The fungicidal compositions according to the invention for which the compound (I) is the compound of formula (I) in which M is a sulphur atom and n is equal to 0, also known as (4S)4-methyl-2-methylthio-4-phenyl-1-phenylamino-2-imidazolin-5-one, are preferred.

In the compositions according to the invention, the compound (I)/compound (II) ratio is advantageously chosen so as to produce a synergistic effect. The term synergistic effect is understood to refer in particular to that defined by Colby S.R. in an article entitled "Calculation of the synergistic and antagonistic responses of herbicide combinations" published in the journal Weeds, 1967, 15, p. 20–22. The said article uses the formula:

$$E=X+Y-XY/100$$

in which E represents the expected percentage of inhibition of the disease for the combination of the two fungicides at defined doses (for example equal to x and y respectively), X is the percentage of inhibition observed for the disease by the compound (I) at a defined dose (equal to x), Y is the percentage of inhibition observed for the disease by the compound (II) at a defined dose (equal to y). When the percentage of inhibition observed for the combination is greater than E, there is a synergistic effect.

The term synergistic effect is also understood to refer to that defined by application of the Tammes method, "Isoboles, a graphic representation of synergism in pesticides" Netherlands Journal of Plant Pathology, 70 (1964), p. 73–80.

The ranges of the compound (I)/compound (II) ratio indicated above do not in any way limit the scope of the invention, but are rather mentioned as a guide, a person skilled in the art being entirely capable of carrying out routine experimentation in order to find other values of the ratio of doses of these 2 compounds for which a synergistic effect is observed.

The compositions according to the invention, comprising compound (I) and compound (II), present noteworthy synergistic properties.

In accordance with a preferred variant of the compositions according to the invention, the compound (I)/compound (II) ratio is advantageously from 0.01 to 10, preferably from 0.2 to 5 and even more preferably from 0.3 to 3.

In addition to the compound (I) and the compound (II), the compositions according to the invention comprise an agriculturally acceptable inert support and optionally an agriculturally acceptable surfactant. In the following text, the term active material denotes the combination of the compound (I) with the compound (II), and the percentages quoted are, except where otherwise mentioned, weight/weight percentages.

In the present description, the term "support" denotes an organic or inorganic, natural or synthetic material with which the active material is combined in order to facilitate its application onto the plant or onto the soil. This support is thus generally inert and should be agriculturally acceptable, in particular on the crop treated. The support may be solid (in particular: clays, natural or synthetic silicates, silica, resins, waxes, solid fertilisers) or liquid (in particular: water, alcohols, ketones, petroleum fractions, aromatic or paraffinic hydrocarbons, chloro-hydrocarbons, liquefied gases).

The surfactant may be an emulsifying, dispersing or wetting agent of ionic or non-ionic type.

Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyltaurates) and phosphoric esters of polyoxyethylated phenols or alcohols. The presence of at least one surfactant is often required since the active material and/or the inert support are not water-soluble and the vector agent for the application in water.

These compositions may also contain other ingredients of any kind such as, for example, protective colloids, adhesives, thickeners, thixotropic agents, penetration agents, stabilizers, sequestering agents, pigments, dyes or polymers More generally, the compositions according to the invention may be combined with any solid or liquid additives corresponding to the usual techniques of agrochemical formulation.

The application techniques are well known to those skilled in the art and they may be used without inconvenience in the context of the present invention. Mention may be made, for example, of spraying.

Among the compositions, solid or liquid compositions may be mentioned generally.

As forms of solid compositions, mention may be made of powders for dusting or dispersion (with an active material content which may be up to 100%) and granules, in particular those obtained by extrusion, by compacting, by impregnation of a granular support or by granulation of a powder (the active material content in these granules being from 1 to 80% for the latter cases).

The compositions may also be used in the form of a powder for dusting; a composition comprising 50 g of active material, 10 g of finely divided silica, 10 g of organic pigment and 970 g of talc may thus be used; these constituents are mixed together and ground and the mixture is applied by dusting.

As liquid composition forms or forms intended to constitute liquid compositions during application, mention may be made of solutions, in particular water-soluble concentrates, emulsifiable concentrates, emulsions, concentrated suspensions, aerosols, wettable powders (or powder to be sprayed), pastes and dispersible granules.

The emulsifiable or soluble concentrates usually comprise 10 to 80% active material, the ready-to-apply emulsions or solutions themselves containing 0.01 to 20% active material.

For example, in addition to the solvent, the emulsifiable concentrates may contain, whenever necessary, 2 to 20% of suitable additives such as the stabilizers, surfactants, penetration agents, corrosion inhibitors, dyes or adhesives mentioned above.

Starting with these concentrates, emulsions of any desired concentration may be obtained by dilution with water.

The concentrated suspensions, which may also be applied by spraying, are prepared so as to obtain a stable fluid product which doss not separate on settling and they usually contain from 10 to 75% of active material, from 0.5 to 15% of surfactants, from 0.1 to 10% of thixotropic agents, from 0 to 10% of suitable additives, such as pigments, dyes, antifoaming agents, corrosion inhibitors, stabilizers, penetration agents and adhesives and, as support, water or as the compositions of wettable powder type.

As already stated, the aqueous emulsions and dispersions, for example the compositions obtained by diluting a wettable powder or as emulsifiable concentrate according to the invention with water, are included within the general scope of the 10 present invention. The emulsions may be of the water-in-oil or oil-in-water type and they may have a thick consistency such as that of a "mayonnaise".

The fungicidal compositions according to the invention usually contain from 0.5 to 95% of the combination of compound (I) and compound (II).

This may be the concentrated composition, that is to say the commercial product combining compound (I) and compound (II). It may also be the dilute composition ready to be applied to the crops to be treated. In the latter case, the dilution with water may be carried out either using a commercial concentrated composition containing compound (I) and compound (II) (this mixture is referred to as the "ready-to-use" mixture or "ready mix"), or using a mixture prepared at the time of use (known as the "tank mix") of two commercial concentrated compositions each containing compound (I) and compound (II).

Lastly, the subject of the invention is a process for curatively or preventively combating the phytopathogenic fungi of crops, characterised in that an effective and non-phytotoxic amount of a fungicidal composition according to the invention in applied to the vegetation to be treated.

The phytopathogenic fungi of the crops which may be combated by this process are, in particular, those:

of the group of oomycetes:
  of the genus Phytophthora such am *Phytophthora infestans* (mildew of Solanaceae, in particular late blight of potato or tomato mildew),
  of the family of Peronosporaceae, in particular *Plasmopara viticola* (downy mildew of grapevine), *Plasmopara halstodei* (sunflower mildew), *Pseudoperonospora sp* (in particular cucurbit mildew and downy mildew of hop), *Bremia lactucae* (mildew of lettuce), *Peronospora tabacinae* (downy mildew of tobacco) and *Peronospora parasitica* (downy mildew of cabbage), of the group of adelomycetes:
  of the genus Alternaria, for example *Alternaria solani* (early blight of Solanaceae and in particular of tomato and potato),
  of the genus Guignardia, in particular *Guignardia bidwelli* (black rot of grapevine),
  of the genus oidium, for example powdery mildew of grapevine (*Uncinula necator*); powdery mildew of leguminous crops, for example *Erysiphe polygoni* (powdery mildew of Cruciferae): *Leveillula taurica*,

*Erysiphe cichoracearum, Sphaorothaca fuligena* (powdery mildew of cucurbits, of composites and of tomato); *Erysiphe communis* (powdery mildew of beetroot and cabbage); *Erysiphe pisi* (powdery mildew of pea and alfalfa); *Erysiphe polyphaga* (powdery mildew of bean and cucumber mildew); *Erysiphe umbelliferarum* (powdery mildew of umbellifera, in particular of carrot); *Sphaorotheca humuli* (hop mildew).

The expression "are applied to the vegetation to be treated" is understood to mean, for the purposes of the present text, that the fungicidal compositions which form the subject of the invention may be applied by means of various treatment processes such an:

spraying a liquid comprising one of the said compositions onto the aerial parts of the said vegetation, dusting, incorporation of granules or powders into the soil, watering around the said vegetation and, in the case of trees, injection or sprinkling.

The spraying of a liquid onto the aerial parts of the crops to be treated is the preferred treatment process.

The expression "effective and non-phytotoxic amount" is understood to refer to an amount of composition according to the invention which is sufficient to allow the control or destruction of the fungi present or liable to appear on the crops, this amount entailing no symptoms of phytotoxicity for the said crops. Such an amount is liable to vary within a wide range depending on the fungus to be combated, the type of crop, the climatic conditions and the nature of the compound (II) included in the fungicidal composition according to the invention. This amount may be determined by systematic field trials, which are within the capabilities of those skilled in the art.

Under the usual conditions of agricultural practice, an amount of fungicidal composition according to the invention corresponding to a dose of compound (I) of from 10 to 500 g/ha, preferably from 20 to 300 g/ha, generally gives good results.

According to the invention, the amount of fungicidal composition advantageously corresponds to a dose of compound (II) of from 50 to 500 g/ha, preferably from 100 to 300 g/ha.

The example which follows is given purely by way of illustration of the invention, which it does not limit in any way.

In this example, compound (I) is understood to denote (4S)-4-methyl-2-methylthio-4-phenyl-1-phenylamino-2-imidazolin-5-one.

EXAMPLE 1

Field trial of a composition comprising compounds (I) and (II) against late blight of potato (*Phytophthora infestans*):

A composition comprising compound (I) in the form of a concentrated suspension containing 500 g/l and a composition comprising compound (II) in the form of a concentrated suspension containing 240 g/l are used.

These 2 compositions are mixed together so as to obtain a ratio: compound (I)/compound (II) equal to and 1.5.

The mixture is applied, after dilution with water, at a rate of 800 l/ha onto a field of potatoes 40 days after planting the tubers. The doses applied are:

for the ratio 1: 150 g/ha for compound (I) and 150 g/ha for compound (II);

for the ratio 1.5: 150 g/ha for compound (I) and 100 g/ha for compound (II).

This application is repeated 6 times every 7 days.

Two days after the first application, contamination is carried out by spraying spores of *Phytophthora infestans*.

The results are observed 22 days after the 7th application. For this, the contamination C (or degree of attack), expressed by the fraction of foliar surface (expressed in %) having blackish marks corresponding to attack by the disease, is evaluated visually (relative to an untreated plot which is also contaminated).

The efficacy E is calculated according to the Abbott formula

Excellent efficacy results were obtained with a synergistic effect.

A neighbouring plot treated with mancozeb at a rate of 1600 g/ha gave rise to an efficacy of about one-half.

What is claimed is:

1. Fungicidal compositions comprising synergistic fungicidally effective amounts of a compound (I) of formula:

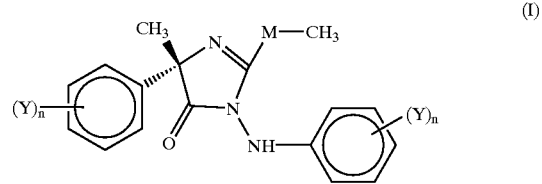

(I)

in which:
M represents an oxygen or sulphur atom;
n is an integer equal to 0 or 1;
Y is a fluorine or chlorine atom or a methyl radical;
and a compound (II) which is N-[3'-(1'-chloro-3'-methyl-2'-oxopentan)]-3,5-dichloro-4-methylbenzamide;
wherein
the compound (I)/compound (II) ratio by weight is from 0.01 to 50.

2. Fungicidal compositions according to claim 1, wherein the compound (I) is (4S)-4-methyl-2-methylthio-4-phenyl-1-phenylamino-2-imidazolin-5-one.

3. Fungicidal compositions according to claim 1, wherein the compound (I)/compound (II) ratio is from 0.01 to 10.

4. Fungicidal compositions according to claim 1, wherein they comprise, in addition to the compounds (II) and (II), an agriculturally acceptable inert support and/or optionally an agriculturally acceptable surfactant.

5. A fungicidal composition according to claim 1, wherein the composition comprises from 0.5 to 95% of the combination of compound (I) and compound (II).

6. A product comprising synergistic fundicidally effective amounts of a compound (I) of formula:

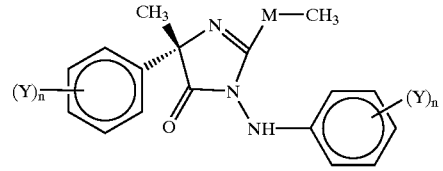

in which:
M represents an oxygen or sulphur atom;
n is an integer equal to 0 or 1;
Y is a fluorine or chlorine atom or a methyl radical;
and a compound (II) which is N-[3'-(1'-chloro-3'-methyl-2'-oxopentan)]-3,5-dichloro-4-methylbenzamide;
wherein the compound (I)/compound (II) ratio by weight is from 0.01 to 50, as a combined preparation for simultaneous, separate or sequential use in combating phytopathogenic fungi of crops at a locus.

7. Fungicidal compositions according to claim 1, wherein the compound (I)/compound (II) ratio by weight is from 0.1 to 10.

8. Fungicidal compositions according to claim 1, wherein the compound (I)/compound (II) ratio by weight is from 0.2 to 5.

9. Fungicidal compositions according to claim 1, wherein the compound (I)/compound (II) ratio by weight is from 0.3 to 3.

10. A product according to claim 6, wherein the compound (I)/compound (II) ratio by weight is from 0.1 to 10.

11. A process for combating phytopathogenic fungi of crops at a locus which comprises applying thereto an effective and non-phytotoxic amount of a fungicidal composition according to claim 1.

12. A process for curatively or preventively combating the phytopathogenic fungi of crops, wherein an effective and non-phytotoxic amount of a fungicidal composition according to claim 1 is applied to the crops to be treated.

13. Process according to claim 12, wherein the fungicidal composition is in liquid form and is applied by spraying the liquid onto the aerial parts of the crops to be treated.

14. Process according to claim 12, wherein the amount of the fungicidal composition corresponds to a dose of compound (I) of from 10 to 500 g/ha.

15. Process according to claim 12, wherein the amount of the fungicidal composition corresponds to a dose of compound (I) of from 20 to 300 g/ha.

16. A process for combating phytopathogenic fungi of crops at a locus which comprises applying thereto a fungicidal composition according to claim 7.

17. A process for curatively or preventively combating the phytopathogenic fungi of crops, wherein an effective and non-phytotoxic amount of a fungicidal composition according to claim 7 is applied to the crops to be treated.

18. Process according to claim 12, wherein the amount of the fungicidal composition corresponds to a dose of compound (II) of from 50 to 500 g/ha.

19. Process according to claim 12, wherein the amount of the fungicidal composition corresponds to a dose of compound (II) of from 100 to 300 g/ha.

* * * * *

UNITED STATES PATENT AND TRADEMARK OFFICE
CERTIFICATE OF CORRECTION

PATENT NO. : 6,417,216 B1
DATED : July 9, 2002
INVENTOR(S) : Chazalet et al.

It is certified that error appears in the above-identified patent and that said Letters Patent is hereby corrected as shown below:

Column 6,
Line 44, delete "(II) and (II)" and insert -- (I) and (II) --.

Signed and Sealed this

Nineteenth Day of November, 2002

Attest:

Attesting Officer

JAMES E. ROGAN
Director of the United States Patent and Trademark Office